(12) United States Patent
Yako et al.

(10) Patent No.: US 10,029,654 B2
(45) Date of Patent: Jul. 24, 2018

(54) ENHANCED VEHICLE CLEANING

(71) Applicant: Ford Global Technologies, LLC, Dearborn, MI (US)

(72) Inventors: Sarra Awad Yako, Allen Park, MI (US); Daniel Denomme, Farmington Hills, MI (US); Sandro Nuesch, Ann Arbor, MI (US); Samuel Hooson, Royal Oak, MI (US)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 0 days.

(21) Appl. No.: 15/097,443

(22) Filed: Apr. 13, 2016

(65) Prior Publication Data
US 2017/0297537 A1 Oct. 19, 2017

(51) Int. Cl.
*B60S 1/64* (2006.01)
*B60N 2/44* (2006.01)
*B08B 3/02* (2006.01)
*B60N 2/90* (2018.01)

(52) U.S. Cl.
CPC ............ *B60S 1/64* (2013.01); *B08B 3/024* (2013.01); *B60N 2/90* (2018.02)

(58) Field of Classification Search
CPC .. B60S 1/64; B08B 3/024; B60N 2/44; B60N 2/90
USPC .......................................................... 296/63
See application file for complete search history.

(56) References Cited

U.S. PATENT DOCUMENTS

| 6,459,955 | B1 * | 10/2002 | Bartsch | ..................... | A47L 9/00 |
| | | | | | 318/568.11 |
| 6,926,601 | B2 * | 8/2005 | Aoki | ......................... | A61L 9/16 |
| | | | | | 454/121 |
| 7,266,859 | B2 * | 9/2007 | Slone | ......................... | B60S 1/64 |
| | | | | | 15/313 |
| 8,437,875 | B2 * | 5/2013 | Hernandez | ........... | G05D 1/0217 |
| | | | | | 134/172 |
| 2004/0107528 | A1 * | 6/2004 | LeClear | .................... | A47L 5/38 |
| | | | | | 15/313 |
| 2004/0107258 | A1 | 7/2004 | LeClear et al. | | |
| 2009/0019662 | A1 | 1/2009 | Yona et al. | | |
| 2012/0189490 | A1 | 7/2012 | Van den bossche et al. | | |
| 2012/0210536 | A1 * | 8/2012 | Jan | ............................ | B60S 1/64 |
| | | | | | 15/313 |
| 2012/0264361 | A1 | 10/2012 | Scheer et al. | | |

FOREIGN PATENT DOCUMENTS

JP 2010235041 A 10/2010

* cited by examiner

Primary Examiner — Joseph D. Pape
Assistant Examiner — Dana D Ivey
(74) Attorney, Agent, or Firm — Frank A. MacKenzie; Bejin Bieneman PLC

(57) ABSTRACT

A cleaning apparatus is actuated to move At least one object from a vehicle floor to a container. A vehicle seat is sprayed with a cleaning fluid from a nozzle.

19 Claims, 13 Drawing Sheets

ENHANCED VEHICLE CLEANING

BACKGROUND

Autonomous vehicles may be used in ride-sharing services to transport users. Users (i.e., shared vehicle riders occupying the shared vehicle) may soil or litter a vehicle interior, e.g., by spilling food or beverages, or may leave litter or trash on vehicle seats after exiting the vehicle. Subsequent users may not want to use the vehicle after such soiling or littering. Further, waste or the like left in a vehicle, e.g., on vehicle seats, may result in unsanitary conditions in a vehicle interior.

DETAILED DESCRIPTION

A system for cleaning a vehicle between uses by different sets of users cleans the vehicle when one set of one or more users leaves the vehicle, presenting a second set of one or more users with a cleaned vehicle. The system can include a bar and/or cleaning arms that push trash off a vehicle seat and onto a vehicle floor. The bar may include a nozzle to spray a sanitizer on vehicle seats. The system can further include a vacuum device to collect the trash from the floor and move the trash to an area for trash collection. For example, the system can include a trash compactor that compresses trash received from the cleaning arm and/or vacuum device. Thus, the system cleans and/or sanitizes a shared vehicle.

Figure 1:
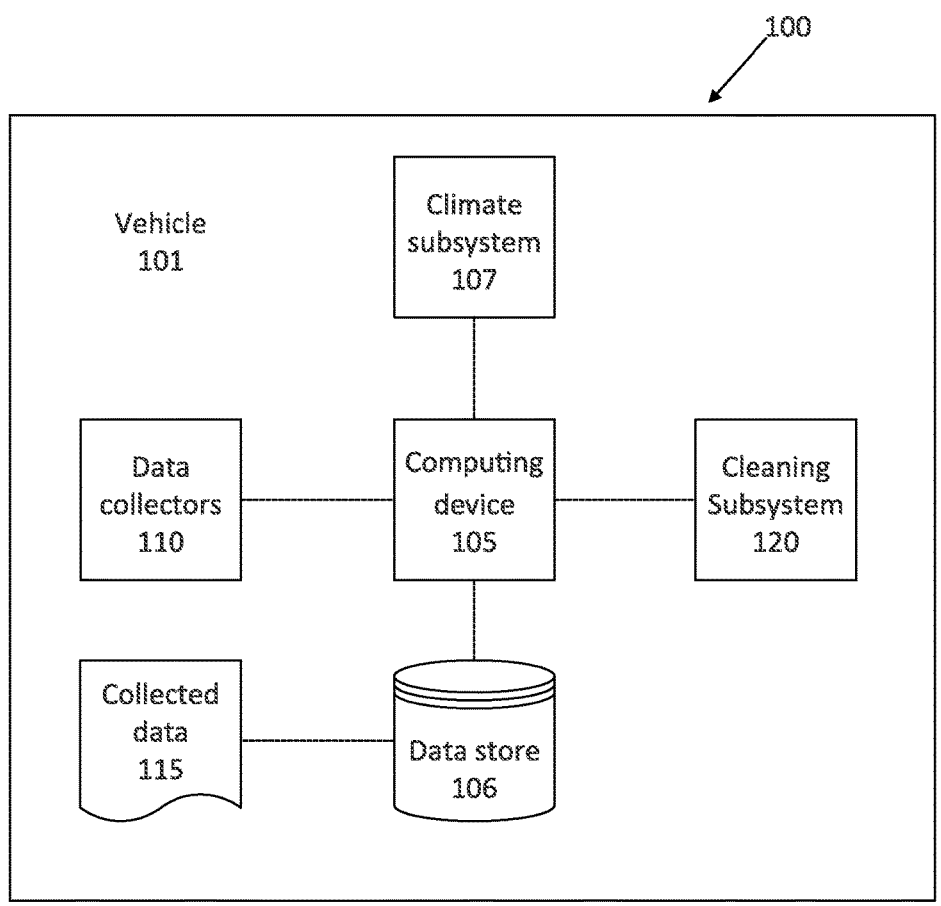
FIG. 1 is a block diagram of an example vehicle cleaning system.

FIG. 1 illustrates a vehicle 101 cleaning system 100. The vehicle 101 includes a computing device 105. The computing device 105 is programmed to receive collected data 115 from one or more data collectors 110, e.g., vehicle 101 sensors, concerning various metrics related to the vehicle 101. For example, the metrics may include location of vehicle 101 users, presence of trash, refuse, litter, dirt, spilled liquid, etc. Further examples of such metrics may include measurements of vehicle systems and/or components (e.g. a steering system, a powertrain system, a brake system, internal sensing, external sensing, etc.).

The computing device 105 is generally programmed for communications on a vehicle 101 network, e.g., an Ethernet, a controller area network (CAN) bus, or the like. The computing device 105 may also have a connection to an onboard diagnostics connector (OBD-II). Via the CAN bus, OBD-II, and/or other wired or wireless mechanisms, the computing device 105 may transmit messages to various devices in a vehicle and/or receive messages from the various devices, e.g., controllers, actuators, sensors, etc., including data collectors 110. Alternatively or additionally, in cases where the computing device 105 actually comprises multiple devices, vehicle network may be used for communications between devices represented as the computing device 105 in this disclosure.

The computing device 105 is communicatively connected to a data store 106. The data store 106 may be of any known type, e.g., hard disk drives, solid-state drives, servers, or any volatile or non-volatile media. The data store 106 may store collected data 115 sent from data collectors 110.

The system 100 may include a climate control subsystem 107. The climate control subsystem 107 may be programmed to heat or cool intake air and introduce the heated or cooled air into the interior of the vehicle 101. The climate control subsystem 107 may include a fan to move air throughout the interior of the vehicle 101.

The system 100 may include a plurality of data collectors 110. The data collectors 110 may include a variety of devices. For example, various controllers in a vehicle may operate as data collectors 110 to provide data 115 via the CAN bus, e.g., data 115 relating to user presence, system and/or component functionality, etc. Sensor data collectors 110 could include mechanisms such as RADAR, LIDAR, sonar, etc. sensors that could be deployed to determine location of an object, e.g., trash. Yet other data collectors 110 could include cameras, breathalyzers, motion detectors, biometric sensors, seat weight sensors, door sensors, seatbelt sensors i.e., data collectors 110 to provide data 115 for determining whether the users are present in the vehicle 101.

Collected data 115 may include a variety of data collected in a vehicle 101. Examples of collected data 115 are provided above, and moreover, data 115 is generally collected using one or more data collectors 110, and may additionally include data calculated therefrom in the computing device 105. In general, collected data 115 may include any data that may be gathered by the data collectors 110 and/or computed from such data.

The system 100 may include a cleaning subsystem 120. The cleaning subsystem 120 may receive instructions from the computing device 105 to actuate components arranged to clean the vehicle 101, e.g., a cleaning apparatus 130, a vacuum device 135, a trash compactor 140, etc. For example, the cleaning subsystem 120 can, by actuating arms 170 and/or a bar 180 via an actuator 175, push items such as trash 165 off of vehicle seats 125 and onto a vehicle floor 150. The cleaning subsystem 120 can spray a sanitizer on the seats 125 through nozzles 195. As described below, the example cleaning subsystems 120', 120'', 120''', 120'''' are collectively referred to as "the cleaning subsystem 120."

Figure 2:
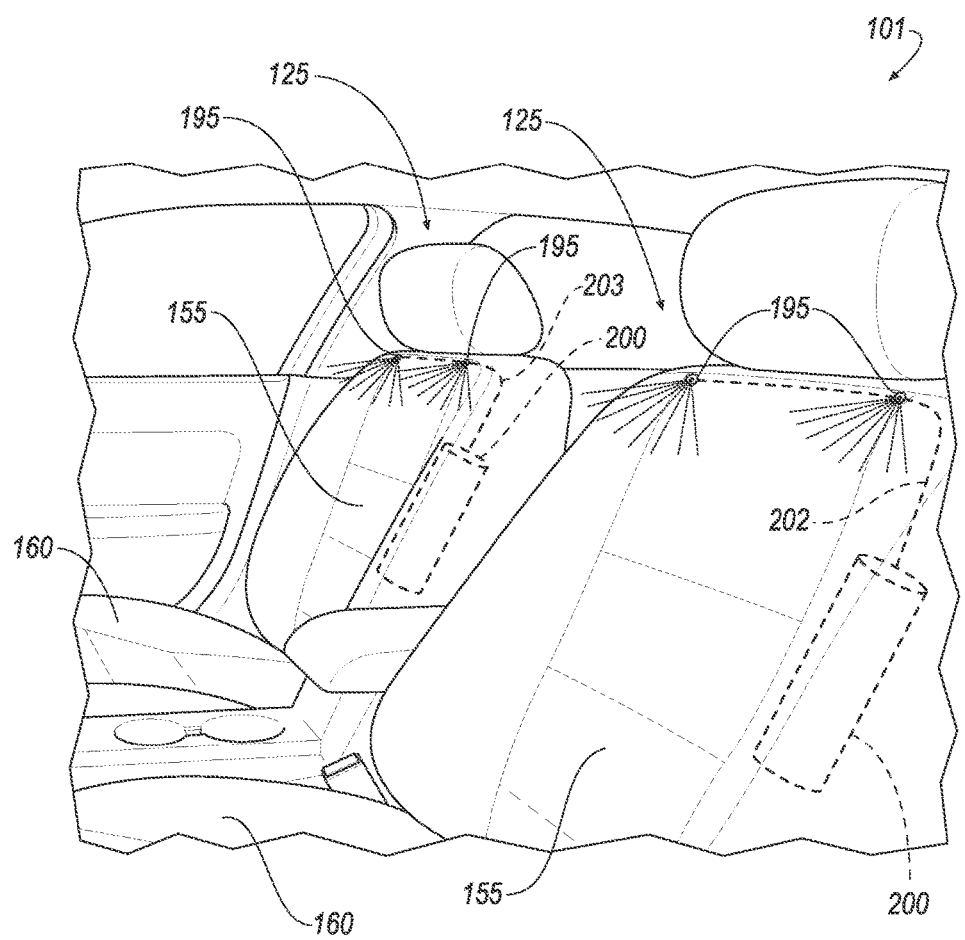
FIG. 2 is a perspective view of an example vehicle seat in a vehicle that includes the system of FIG. 1.

FIG. 2 illustrates an example interior of a vehicle 101. The vehicle 101 includes a plurality of vehicle seats 125. The seats 125 each typically include a seat back 155 and a seat bottom 160. The seat 125 support the users in the vehicle 101. In the example of FIG. 2, the seats 125 are front seats 125 of the vehicle 101, i.e., seats 125 closest to a front end of the vehicle 101. Seat 125 could be in other configurations than shown in the present figures, e.g., rotated to face a side or back of the vehicle 101.

The seats 125 may include and/or have mounted thereon, at least one nozzle 195. The nozzles 195 are arranged to spray a fluid such as a sanitizer or cleaning fluid onto vehicle

101 components, including, e.g., the seats 125, a door panel, a center console, a set of power door and window buttons, a user interface area, etc. In the example of FIG. 2, the nozzles 195 open from a top of the vehicle seat 125, spraying the sanitizer onto the seat back 155 and seat bottom 160. The nozzles 195 are in fluid communication with a fluid supply 200. For example, hoses 202 or the like can run from the fluid supply 200 to supply fluid such as sanitizer that the nozzles 195 can spray on the seats 125. The fluid supply 200 may be a canister or the like disposed in the vehicle seat 125. After the nozzles 195 sprays fluid onto the seats 125, the computing device 105 can actuate the climate control subsystem 107, i.e., actuate the fan, to circulate air to dry the fluid and to ventilate the vehicle cabin to remove or reduce fumes, odors, etc., from the fluid. The nozzles 195 may alternatively be installed on a back of a vehicle seat headrest (not shown).

Figure 3:
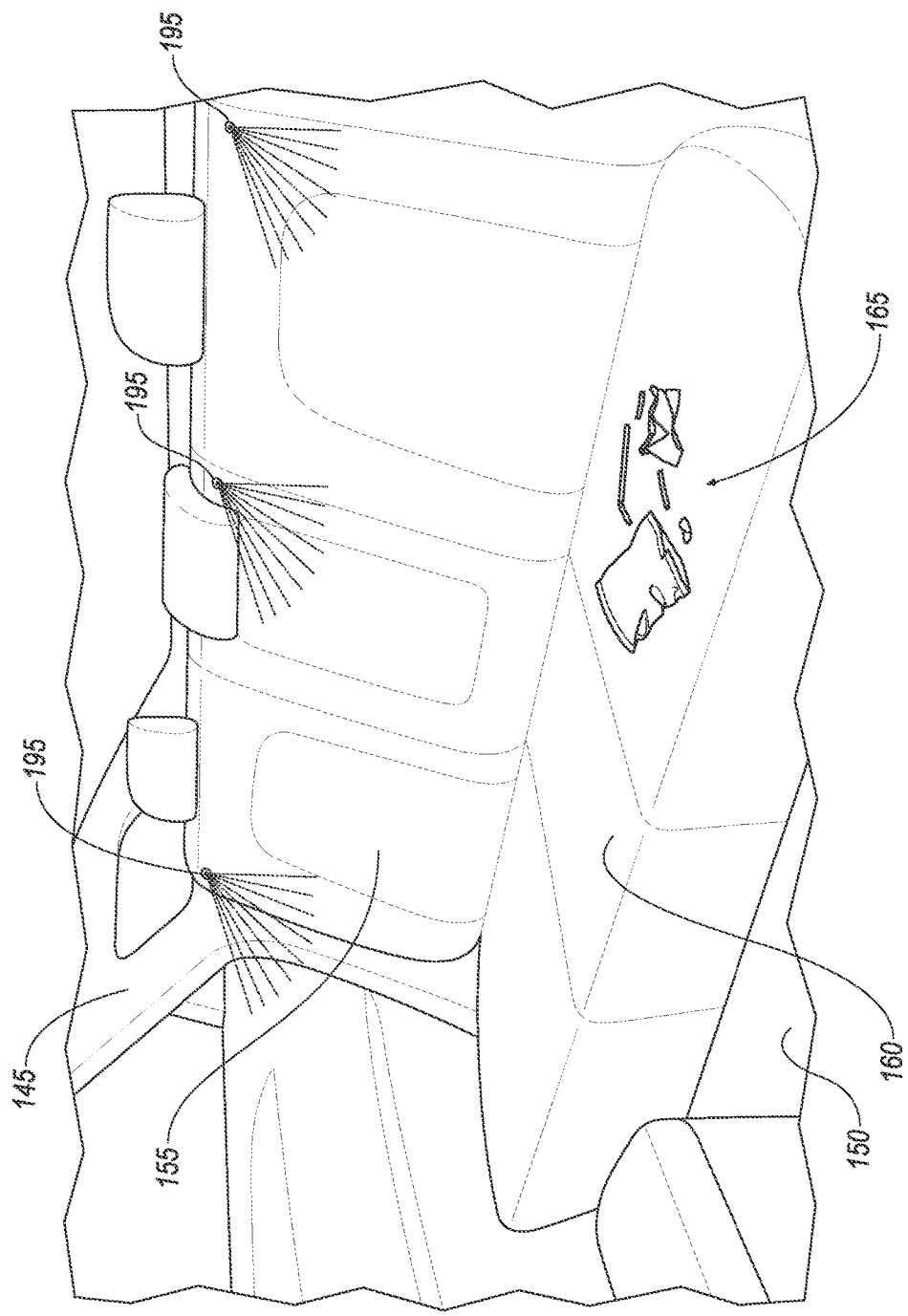
FIG. 3 is a perspective view of a second example of a vehicle seat including a cleaning subsystem that could be used in the system of FIG. 1.

FIG. 3 illustrates another example of an interior of a vehicle 101. The vehicle 101 includes a plurality of vehicle seats 125, a pillar 145, and a floor 150. Here, the seats 125 are rear seats 125 of the vehicle 101, i.e., the seats 125 closest to a rear end of the vehicle 101. Users can leave trash 165 on the seats 125 and the floor 150 when departing from the vehicle 101. As used herein, "trash" 165 refers collectively to one or more objects left in the vehicle 101 after the users leave the vehicle 101, and in addition to refuse, litter, and the like, could refer to other objects. The cleaning subsystem 120 may clean the vehicle 101, i.e., remove the trash 165 from the seats 125 and the floor 150 and sanitize the seats 125. As in the example of FIG. 2, the seats 125 include nozzles 195 to spray the cleaning fluid onto the seats 125.

Figure 4A:
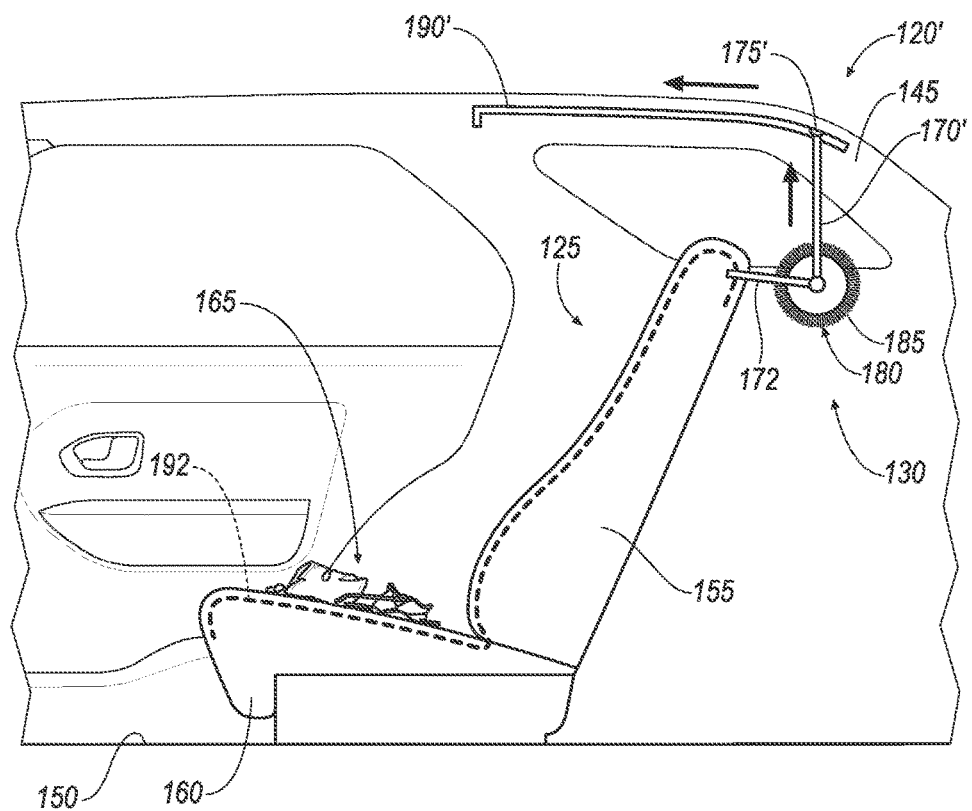
FIGS. 4A-4C are side views of the cleaning subsystem of FIG. 3.
Figure 4B:
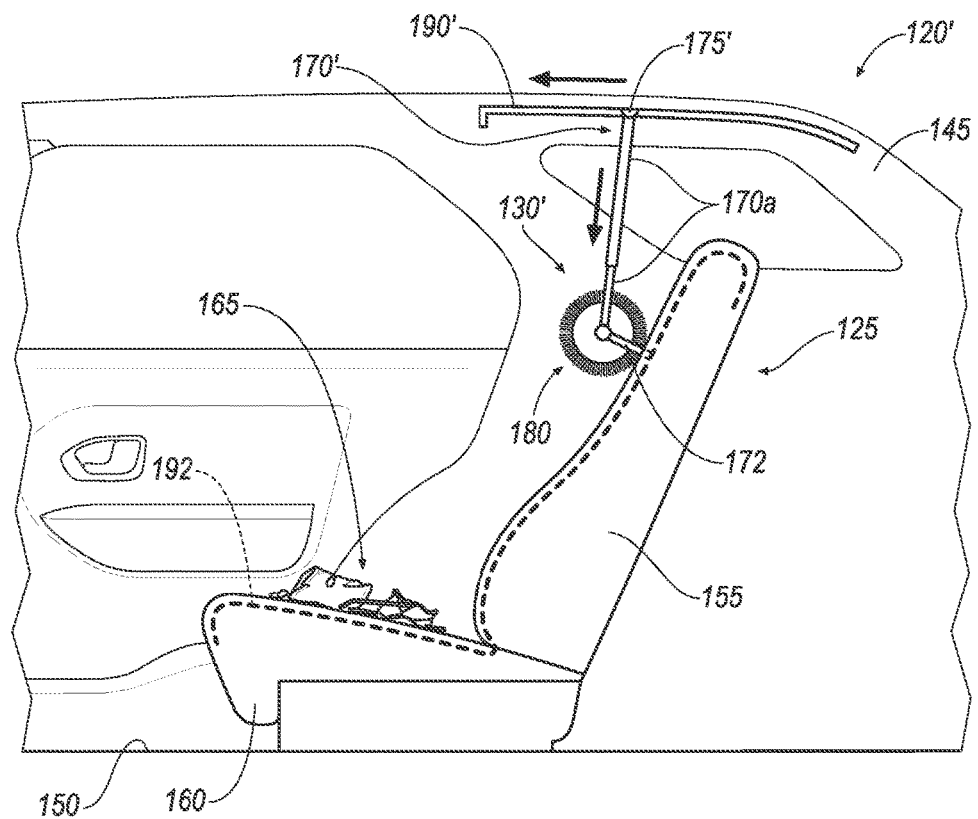
Figure 4C:
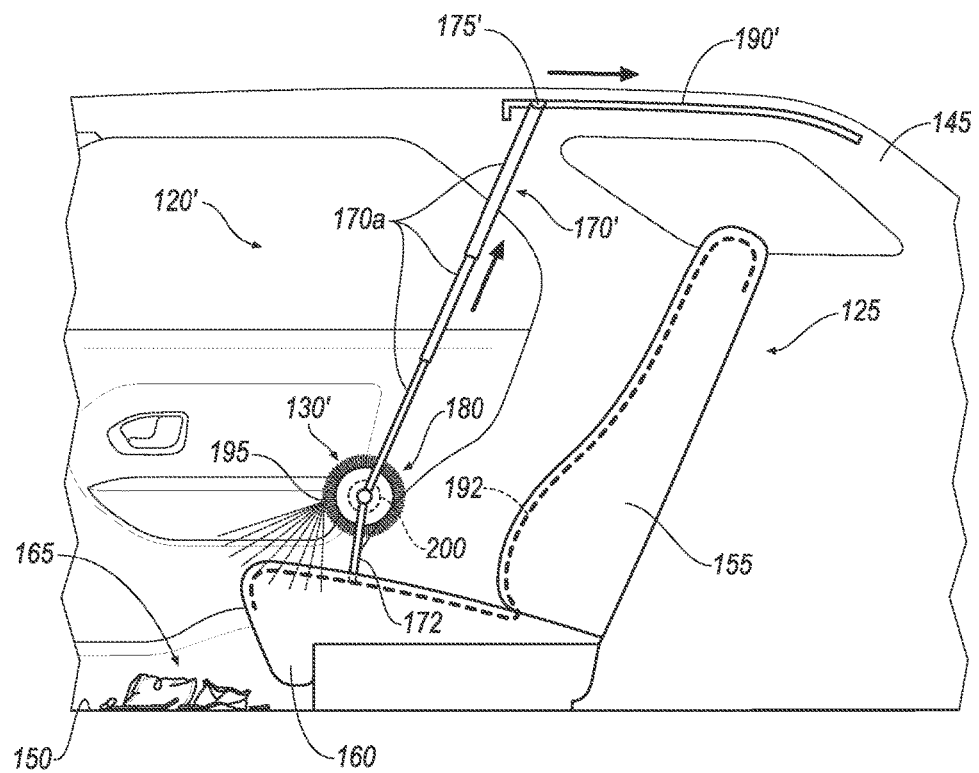

FIGS. 4A-4C illustrate an example cleaning subsystem 120' installed in the vehicle 101. The cleaning subsystem 120' includes a cleaning apparatus 130' arranged to clean the interior of the vehicle 101. The cleaning apparatus 130' is arranged to push trash 165 off of the seats 125 and onto the floor 150.

The cleaning apparatus 130' includes at least one arm 170'. In the example of FIG. 4A-4C, the cleaning apparatus 130' shows one arm 170', but the cleaning apparatus 130 may include one or more second arms 170'. The arms 170' may be stowed behind the seat 125 mounted to the pillar 145. The arms 170' may include a plurality of telescoping sections 170a that allow the arms 170' to extend down the length of the seat backs 155. The sections 170a may be concentric hollow tubes telescopically connected to form the arm 170'. In the example of FIGS. 4A-4C, the arm 170' has three sections 170a. The arms 170', 170'' are collectively referred to as "the arm 170."

The cleaning subsystem 120' includes at least one actuator 175'. The actuator 175' is housed in the pillar 145 and drives the arms 170' along a track 190' in the pillar 145, which moves the cleaning apparatus 130 onto the seats 125. The track 190' is, e.g., a slot in the pillar 145 that allows the arms 170' to move along a length of the pillar 145. The actuator 175' may drive the arms 170' along the seat bottoms 160, pushing the trash 165 from the seat bottoms 160 to the floor 150. At least one of the sections 170a may be movably connected to the actuator 175' so that the sections 170a extend and lengthen the arm 170' to move down the seat 125. The actuator 175' may be, e.g., a motor, a solenoid, a linear track actuator, etc. In the example of FIGS. 4A-4C, the actuator 175' can be a linear track actuator arranged to move the arm 170 along the track 190'. In the following Figures, the actuators 175', 175'', 175''', 175'''' are collectively referred to as "the actuator 175." Furthermore, the tracks 190', 190'', 190''', 190'''' are collectively referred to as "the track 190."

The cleaning apparatus 130' includes a bar 180 connected to at least one of the arms 170'. The bar 180 may be stowed behind the seat 125, as shown in FIG. 4A. The bar 180 is arranged to move down the seats 125, pushing trash 165 off the seats 125 and onto the floor 150, as shown in FIGS. 4B-4C. The bar 180 may extend across a length of the seats 125 between the vehicle 101 doors to push the trash 165 from all seats 125. One of the sections 170a may be rotatably connected to the bar 180 such that when the sections 170a extend, the bar 180 extends down the seat 125. That is, one of the bar 180 and the track 190' includes a pneumatic actuator 175' arranged to extend the sections 170a as the bar 180 extends down the seat 125. The bar 180 may be movably connected to a track 192 in the seat 125 with a positioning arm 172. The track 192 is a slot in the seat 125 that allows the arm 172 to move along the seat 125. The positioning arm 172 is arranged to hold the bar 180 against the seat back 155, and the arm 170' is arranged to be driven by the actuator 175'. That is, the arm 170' drives the bar 180 while the positioning arm 172 positions the bar 180 to push the trash 165 onto the floor 150.

The bar 180 may include a plurality of bristles 185 that collect trash 165. The bristles 185 may be resilient strands such as are known, e.g., made of a polymer, attached to the bar 180 arranged to collect trash 165. As the arms 170' move the bar 180 down the seats 125, the bristles 185 may collect, e.g., sweep, trash 165 from the seats 125. The bristles 185 may also dislodge trash 165 that the bar 180 is unable to reach, e.g., between the seat bottom 160 and the seat back 155.

FIG. 4B shows the cleaning apparatus 130 moving along the seat 125. In this example, the actuator 175' moves along the track 190' and extends the telescoping arm 170' to move the bar 180 down the seat back 155. Further, the positioning arm 172 holds the bar 180 against the seat back 155 and the track 192. In the example of FIG. 4B, the actuator 175' extends the arm 170' to show two sections 170a, one section 170a fully extended, and the other section 170a partially extended. The bar 180 extends down the seat back 155 and the seat bottom 160, pushing the trash 165 onto the floor 150.

Figure 5:
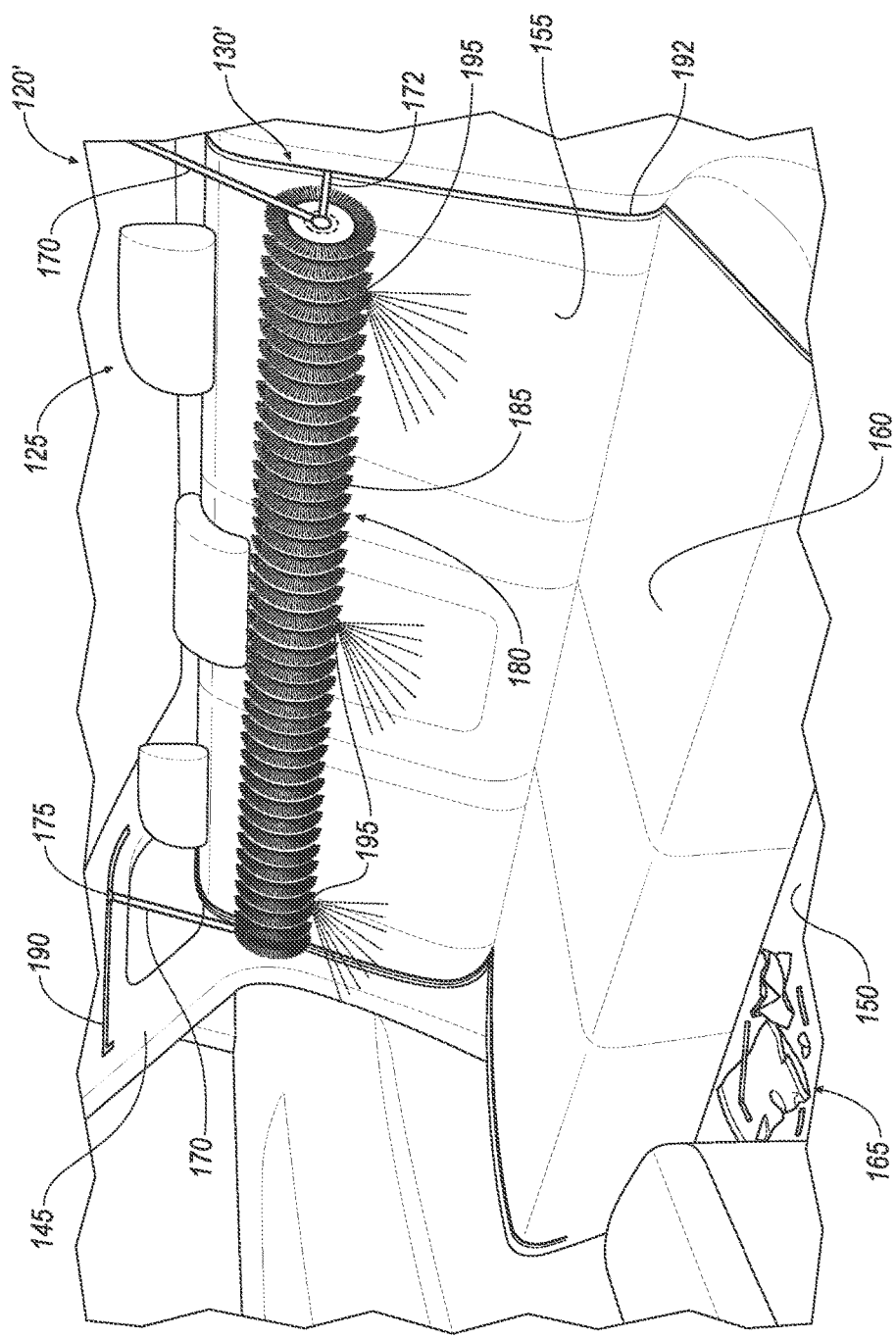
FIG. 5 is a perspective view of the subsystem of FIGS. 4A-4C.

FIG. 4C shows the cleaning apparatus 130 after pushing the trash 165 onto the floor 150. The actuator 175' extends the telescoping arm 170' such that all three sections 170a are extended, allowing the bar 180 to reach the seat bottom 160. After pushing the trash 165 onto the floor 150, the actuator 175' moves along the track 190' back toward the rear of the vehicle 101, pulling the bar 180 and the positioning arm 172 along the track 192 and up the seat back 155. As the bar 180 is pulled along the track 192, the nozzles 195 spray sanitizer onto the seat bottom 160 and the seat back 155. The actuator 175' moves the bar 180 behind the seat 125. While the example seats 125 of FIGS. 2-3 included nozzles 195 arranged in the seats 125, in the example cleaning subsystem 120' of FIGS. 4A-5, the nozzles 195 are arranged in the bar 180 (shown only in FIGS. 4C and 5). While only one nozzle 195 is shown in the side view of FIG. 4C, the example of FIGS. 4A-5 includes three nozzles 195, as shown in FIG. 5. The cleaning subsystem 120 may include a different number of nozzles 195 installed in the bar 180 and/or the seats 125. Further, the nozzles 195 may be arranged to spray fluid such as sanitizer when the bar 180 is at different positions on the seat 125, e.g., on the seat bottom 160, at a position where the seat back 155 and the seat bottom 160 meet, at the top of the seat back 155, etc. The bar 180 may include the fluid supply 200 to deliver sanitizer to the nozzles 195.

FIG. 5 illustrates a perspective view of the cleaning apparatus 130' shown in FIGS. 4A-4C. In this example, the bar 180 has pushed the trash 165 onto the floor 150, and the actuators 175' move the arms 170' along the track 190' to move the bar 180 up the seat backs 155. The nozzles 195 spray the cleaning fluid on the seats 125 as the bar 180 moves up the seat backs 155. Further, the three nozzles 195 are shown spraying sanitizer onto the seats 125.

Figure 6:
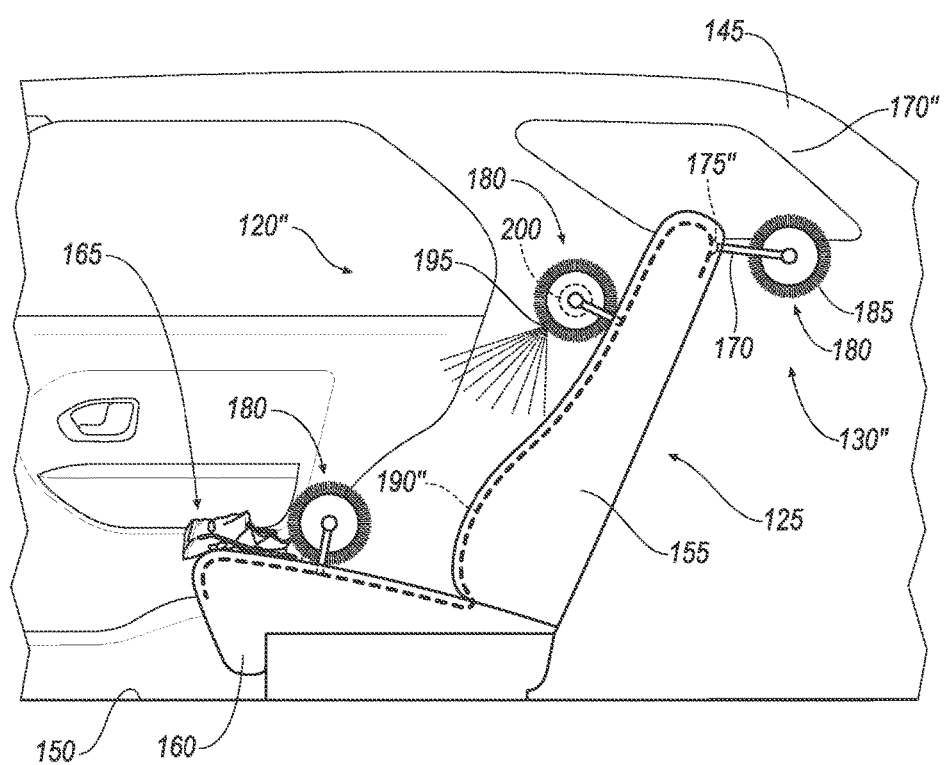
FIG. 6 is a side view of a second example cleaning subsystem that could be used in the system of FIG. 1.

FIG. 6 illustrates a second example cleaning subsystem 120''. In this example, the cleaning apparatus 130 includes arms 170'' attached to the seat 125. That is, while the example of FIGS. 4A-5 includes arms 170' driven along the track 190' in the pillar 145 and the positioning arms 172 driven along the track 192 in the seat 125, the example of FIGS. 6-7 includes arms 170'' driven only along the track 190'' in the seat 125. Thus, the cleaning apparatus 130'' can be installed into the seat 125 rather than in one of the pillars 145.

The cleaning subsystem 120'' includes an actuator 175'' arranged in the seat 125 to drive at least one of the arms 170'' along the track 190'' along the seat 125, moving the bar 180 to push the trash 165 onto the floor 150. While the view in the example of FIG. 6 shows one track 190, the example cleaning subsystem 120 of FIGS. 6-7 includes three tracks 190, shown in the perspective view of FIG. 7. The example of FIG. 6 shows the bar 180 in three example positions: a first position, wherein the bar 180 is disposed behind the seat 125, a second position near a top of the seat back 155, and a third position on the seat bottom 160. The actuator 175'', here, a linear track actuator 175'', drives at least one of the arms 170'' along the track 190'' from the first position to the second and third positions, moving the bar 180 along the seat 125 to push the trash 165 onto the floor 150.

The cleaning apparatus 130 further includes at least one of the nozzles 195 attached to the bar 180. The nozzles 195 may be arranged to spray sanitizer when the bar 180 is in the second position, i.e., when the bar 180 is disposed on the seat back 155. The nozzles 195 may be arranged to spray the sanitizer when the bar 180 is driven down the seat back 155, i.e., from the first position to the third position, or when the bar 180 is driven up the seat back 155, i.e., from the third position to the first position.

Figure 7:
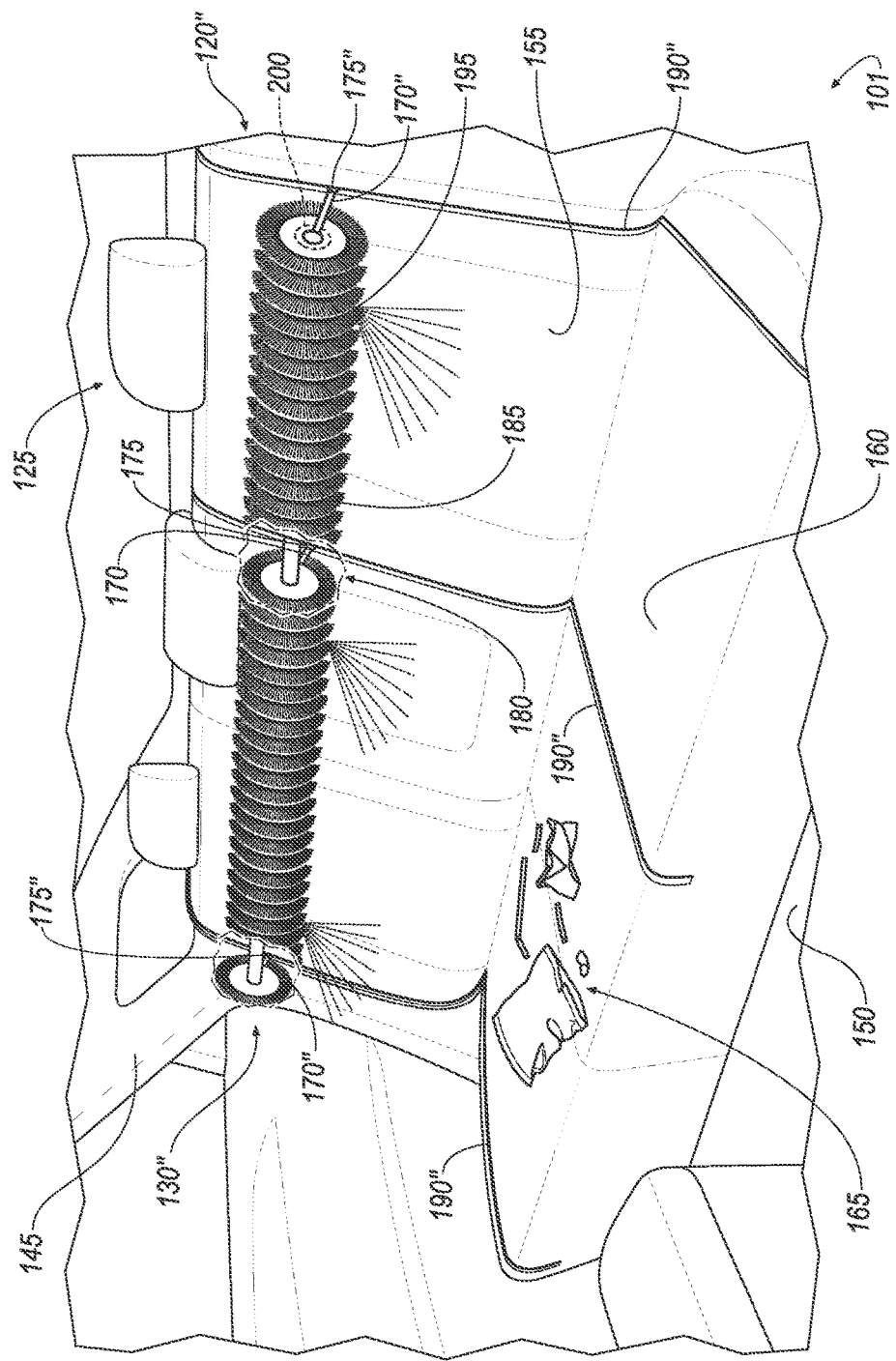
FIG. 7 is a perspective view of the cleaning subsystem of FIG. 6.

FIG. 7 illustrates the interior of the vehicle 101, including the cleaning subsystem 120'' of FIG. 6, in a perspective view. As discussed above, the seats 125 include three tracks 190'' connected to the arms 170'' that support the bar 180. In the example of FIG. 7, each track 190'' including a respective actuator 175'' to move the arm 170'' along the seat. The actuators 175'' move the arm 170'' along the track 190'', which moves the bar 180. The bar 180 is shown in the example of FIG. 7 moving down the seat backs 155 and spraying sanitizer through the nozzles 195.

Figure 8A:
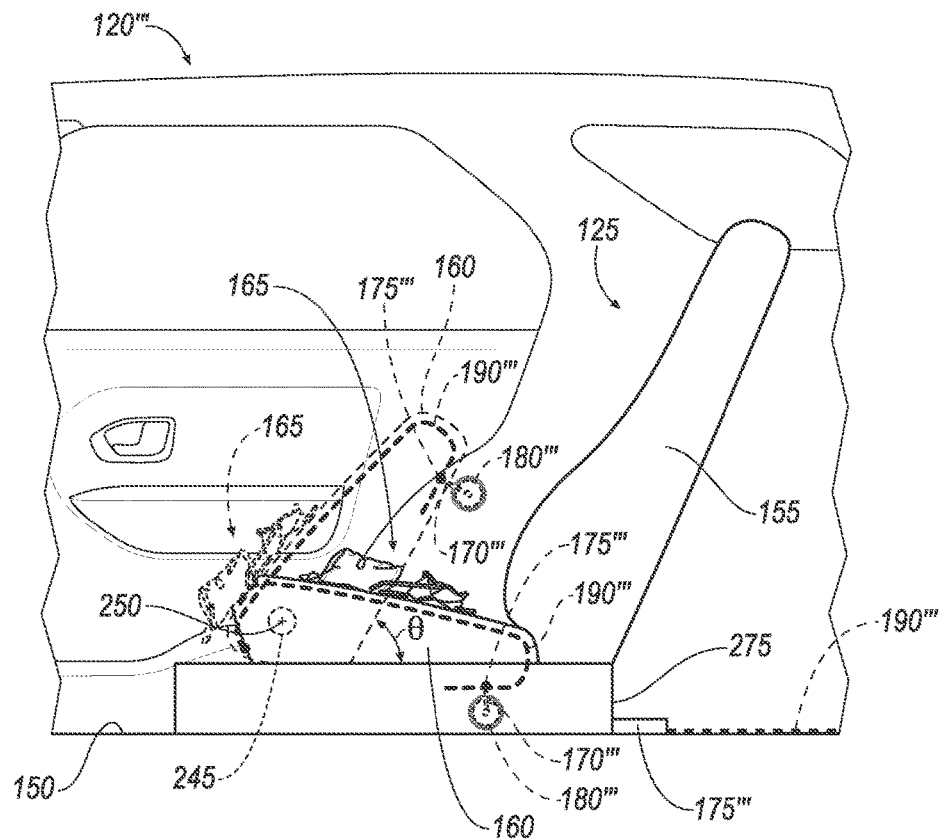
FIGS. 8A-8B illustrate a third cleaning subsystem that could be used in the system of FIG. 1.
Figure 8B:
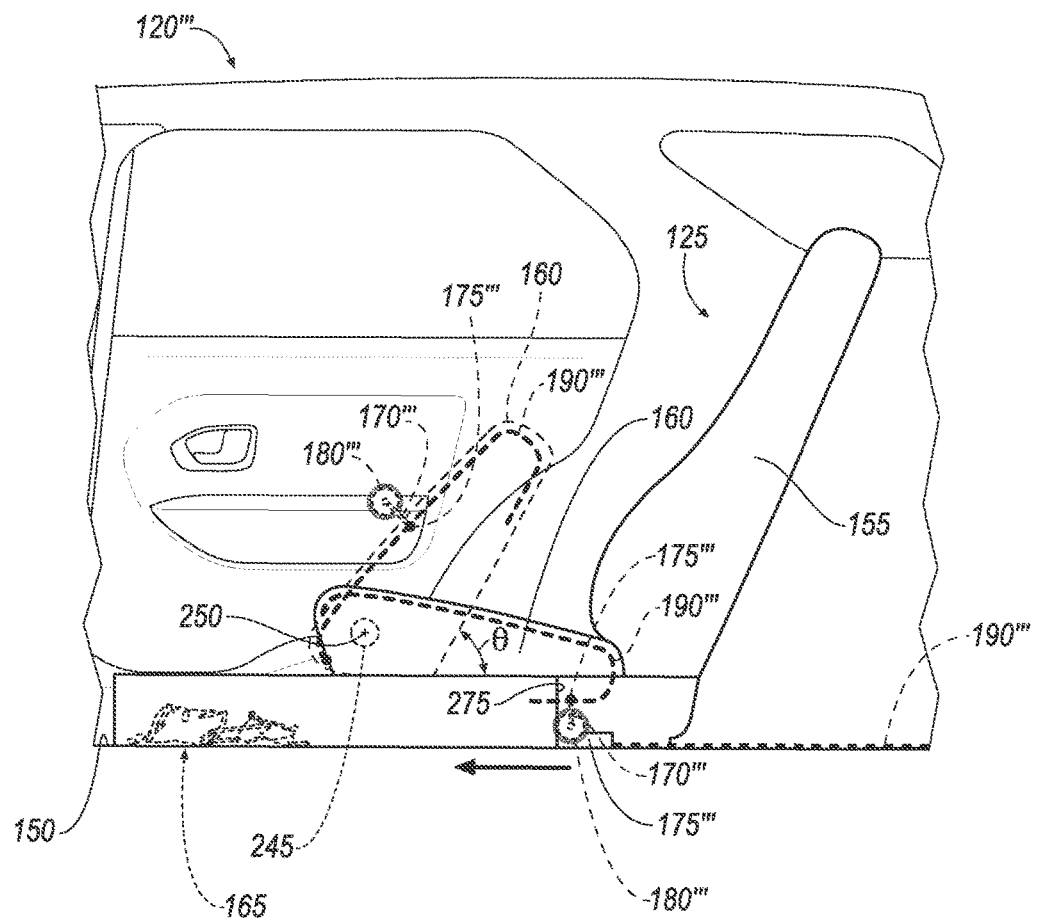

FIGS. 8A-8B illustrates another example cleaning subsystem 120''' including a movable seat bottom 160 for moving trash 165 to the floor 150. The seat 125 includes the seat back 155, which remains stationary, and the movable seat bottom 160 separated from the seat back 155. The seat bottom 160 is rotatably attached to the vehicle 101 body at a pivot point 250. The actuator 245 can be, e.g., a rotary servomotor arranged to rotate the seat bottom 160 about the pivot point 250. The seat bottom 160 then rotates to a predetermined angle θ, allowing trash 165 to fall off of the seat bottom 160 and onto the floor 150. The angle θ can be determined using known methods to allow trash 165 to fall off of the seat bottom 160, e.g., determining a coefficient of friction of the trash 165 with the seat bottom 160 and determining the angle θ as the angle where a gravitational force exceeds a frictional force.

The cleaning subsystem 120''' includes a track 190''' and an actuator 175''' in the seat bottom 160 arranged to move an arm 170''' attached to a bar 180'''. The actuator 175''' moves the bar 180''' along the seat bottom 160, pushing trash 165 off of the seat bottom 160. While the angle θ may be determined to allow the trash 165 to fall off of the seat bottom 160, the bar 180''' can push trash 165 that does not fall off of the seat bottom 160 onto the floor 150. The actuator 175''' is arranged to move the arm 170''' when the seat bottom 160 is rotated to the angle θ.

FIG. 8B shows a movable bin 275 disposed beneath the seat 125. The bin 275 may include another actuator 175''' triggered by the computing device 105. The bin 275 is movably connected to a track 190''' that extends from beneath the seat 125 along the floor 150 to a part of the floor 150 in front of the seat 125. The actuator 245 moves the bin 275 along the track 190''' in front of the seat 125 to receive the trash 165 that falls off the seat bottom 160. The bin 275 may also remain stationary as the seat bottom 160 rotates, receiving trash 165 that falls off of the back of the seat bottom 160. The bar 180''' can push trash 165 into the bin 275 when the trash 165 does not fall off of the seat bottom 160.

Figure 9:
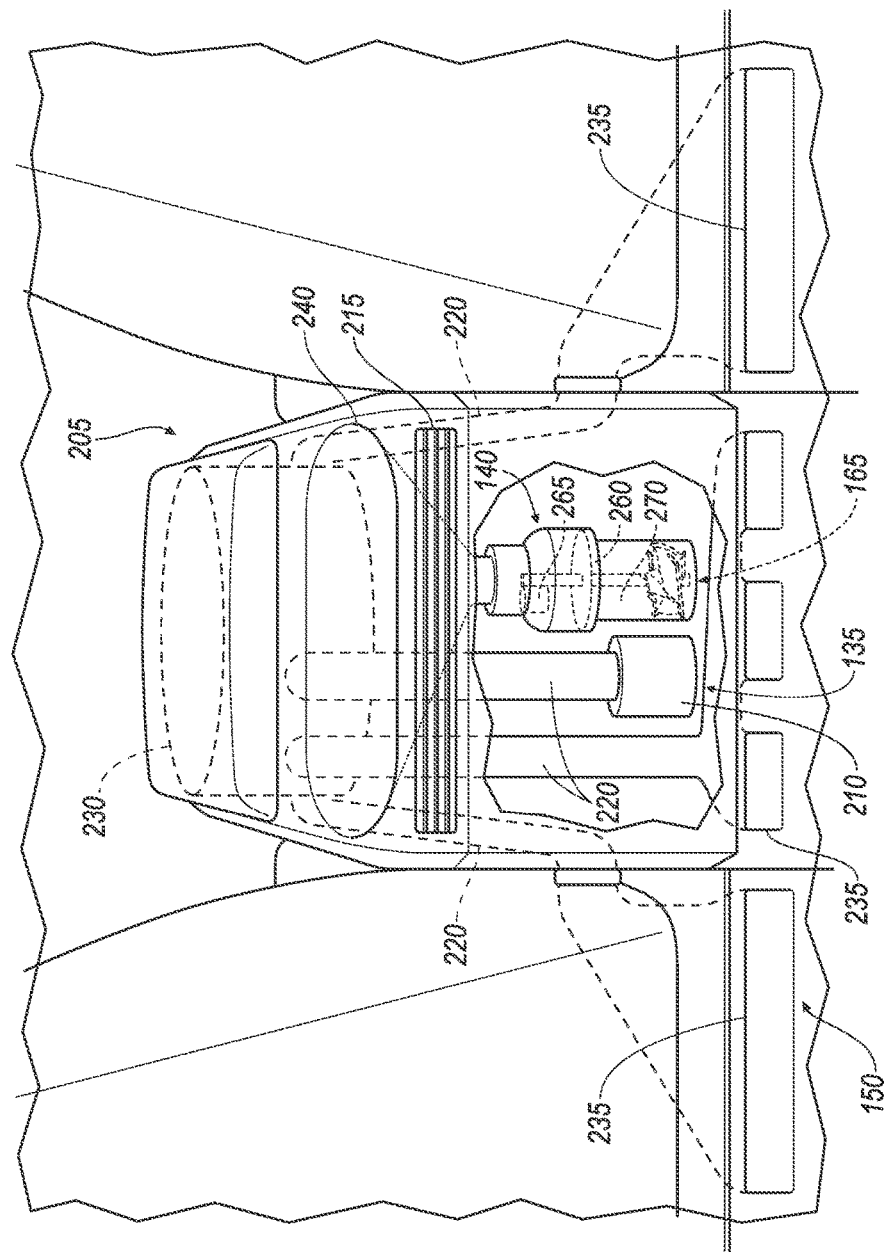
FIG. 9 illustrates an example trash container for collecting trash in a vehicle.

FIG. 9 illustrates an example trash container 205 in the cleaning subsystem 120. The trash container 205 collects the trash 165 from the floor 150. The trash container 205 may be located, e.g., between two front vehicle seats 125 so that users can reach the trash container 205 from any of the seats 125 in the vehicle 101. The trash container 205 may include the trash compactor 140.

The trash container 205 includes a vacuum device 135 to collect the trash 165. The vacuum device 135 collects and moves the trash 165 into the trash container 205. The vacuum device 135 includes a vacuum generator 210. The vacuum generator 210 may be, e.g., an electric motor that rotates a fan, generating a vacuum as the fan pushes air along a fan axial direction. The air that the vacuum generator 210 pushes may include trash 165, which may be directed toward a trash storage bin 230 before the air is expelled through an exhaust port 215. That is, the vacuum generator 210 may push air through the trash storage bin 230, which may include a filter (not shown) to catch the trash 165 and allow the air to continue to the exhaust port 215.

The trash container 205 includes the trash storage bin 230. The trash storage bin 230 is a space in the trash container 205 connected to the vacuum generator 210 and the vacuum ports 235. The trash storage bin 230 collects the trash 165 from the floor 150, removing the trash 165 from sight of the users. That is, the vacuum generator 210 can apply a vacuum across the vacuum ports 235, moving the trash 165 from the floor 150 into the trash storage bin 230. The trash storage bin 230 may include a filter (not shown) to collect the trash 165 in the trash storage bin 230 and allow the air collected by the vacuum to travel out of the exhaust port 215.

The vacuum device 135 may include at least one hose 220 connecting the vacuum generator 210 to the trash storage bin 230 and connecting the trash storage bin 230 to the ports 235. Another hose 220 connects the trash storage bin 230 to the exhaust port 215 to expel air after leaving the trash 165 in the storage bin 230. The hose 220 may be, e.g., a flexible or resilient tube. The hose 220 allows the vacuum generator 210 to remain in the container 205 and collect trash 165 from the floor into the container 205.

The trash container 205 and the seats 125 may include a plurality of vacuum ports 235. The vacuum ports 235 may be openings in the trash container 205 and the seats 125 open to the vacuum generator 210 via the trash storage bin 230 such that the vacuum generator 210 may generate a vacuum through the vacuum ports 235, collecting trash 165 near the trash container 205. The vacuum ports 235 may connect to the trash storage bin 230 via the hoses 220 to move the trash 165 to the trash storage bin 230.

The trash container 205 may define a cavity 240. The cavity 240 can allow users to place trash 165 directly into the trash container 205. The cavity 240 connects to the compactor 140 such that trash 165 placed in the cavity 240 is collected by the compactor 140. The cavity 240 may alternatively be connected to the trash storage bin 230.

The compactor 140 compacts trash 165 collected by the cavity 240. The compactor 140 is generally known and includes a plate 260, a motor 265, and a shaft 270 connecting the plate 260 and the motor 265. The motor 265 rotates the shaft 270, which drives the plate 260 onto the collected trash 165, compressing the trash 165.

Figure 10:
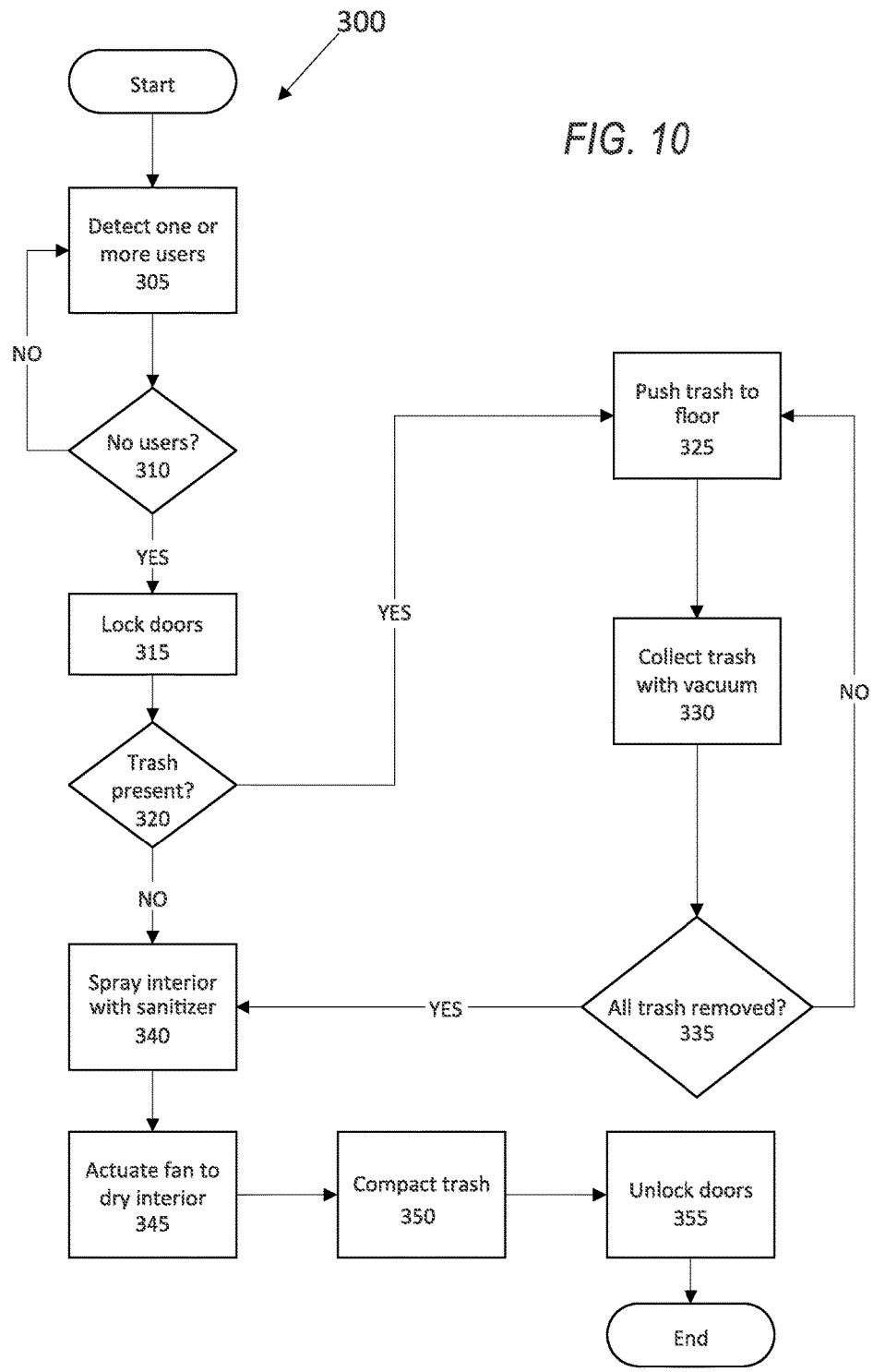
FIG. 10 is a block diagram of an example process for cleaning a vehicle.

FIG. 10 illustrates an example process 300 for cleaning the vehicle 101 with the cleaning subsystem 120. The process 300 starts in a block 305, in which the computing device 105 detects whether one or more users are present in the vehicle 101. The computing device 105 collects data 115 from the data collectors 110 to detect the presence of the users. For example, the computing device 105 may actuate seat weight sensors 110, vision sensors 110, etc.

Next, in a block 310, the computing device 105 determines whether there are one or more users in the vehicle 101 based on the data 115 collected in the block 305. For example, the data 115 from the seat weight sensors 110 may indicate that there are no users in the seats 125. The computing device 105 may be programmed to operate the cleaning subsystem 120 only when the vehicle 101 is empty to ensure that the vehicle 101 is about to collect new users. If the computing device 105 determines that there are no users in the vehicle 101, the process 300 continues in a block 315. Otherwise, the process 300 returns to the block 305.

In the block 315, the computing device 105 actuates a vehicle 101 door lock, as is known, to lock the vehicle 101 doors. Locking the vehicle 101 doors prevents users from entering the vehicle 101 while the cleaning subsystem 120 cleans the vehicle 101.

Next, in the block 320, the computing device 105 determines whether there is any trash 165 present in the vehicle 101. As described above, users may leave trash 165 in the vehicle 101, e.g., on the vehicle seats 125. The computing device 105 can actuate data collectors 110, e.g., vision sensors 110, to collect data 115 to determine whether trash 165 is present in the vehicle 101. If the computing device 105 determines that there is trash 165 in the vehicle 101, the process 300 continues in a block 325. Otherwise, the process continues in a block 340.

In the block 325, the computing device 105 instructs the cleaning subsystem 120 to push the trash 165 to the vehicle floor 150. As described above, the cleaning subsystem 120 may actuate the arm 170 of the cleaning apparatus 130 to push the bar 180 and the brush 185 down the vehicle seat 125 back and across the vehicle seat 125 bottom, pushing the trash 165 off of the vehicle seat 125 and onto the vehicle floor 150. The cleaning subsystem 120 may actuate the arm 170 more than one time, pushing the bar 180 along the seat 125 until all of the trash 165 is on the vehicle floor 150, e.g., until data collectors 110 determine that there is no longer any trash 165 on the vehicle seats 125. In addition or alternatively, the computing device 105 may actuate the actuator 245 to rotate the seat bottom 160, causing the trash 165 to move from the seat bottom 160 and onto at least one of the floor 150 and into the bin 275. The computing device 105 may further actuate the actuator 175''' to move the bar 180''' along the seat bottom 160 when the seat bottom 160 is rotated to the angle $\theta$.

Next, in a block 330, the computing device 105 instructs the cleaning subsystem 120 to collect the trash 165 in the trash container 205. The cleaning subsystem 120 may actuate the vacuum device 135 to apply the vacuum to move the trash 165 from the floor 150 into the trash container 205. For example, as described above, the computing device 105 may actuate the vacuum ports 235 to collect trash 165 near the trash container 205.

Next, in a block 335, the computing device 105 determines whether all of the trash 165 has been removed from the seat 125 and the floor 150. The computing device 105 may actuate data collectors 110 to collect data 115 to determine whether trash 165 remains on at least one of the seats 125. For example, the vision sensors 110 may determine that the vehicle seats 125 have no trash 165 present, the seat weight sensors 110 may detect no weight on the seats 125, etc. If all of the trash 165 has been removed from the seat 125 and the floor 150, the process 300 continues in a block 340. Otherwise, the process 300 returns to the block 325 to move the remaining trash 165 to the floor 150 and collect the trash 165 in the trash container 205.

In the block 340, the computing device 105 instructs the cleaning subsystem 120 to spray the interior of the vehicle 101 with a cleaning fluid such as a sanitizer. As described above, the cleaning apparatus 130 may spray the fluid, e.g., sanitizer, on, e.g., the vehicle seats 125. The cleaning apparatus 130 may spray the sanitizer through the nozzles 195 positioned along the bar 180 and/or in the seats 125.

Next, in a block 345, the computing device 105 actuates the vehicle climate control subsystem 107 to dry the cleaning fluid, which may remain wet after the cleaning subsystem 120 clears the trash from the interior of the vehicle 101. Therefore, the computing device 105 may actuate the climate control subsystem 107, e.g., the fan, to circulate air through the interior of the vehicle 101 to dry the cleaning fluid and provide ventilation to the vehicle 101 cabin.

Next, in a block 350, the computing device 105 instructs the cleaning subsystem 120 to compact the trash 165 with the trash compactor 140. As described above, the cleaning subsystem 120 may actuate the motor 265 to drive the plate 260 along the shaft 270 to compact the trash 165 collected with the cavity 240.

Next, in a block 355, the computing device 105 actuates the vehicle 101 door lock to unlock the vehicle 101 doors in a known manner, and the process 300 ends. The vehicle 101 can thus accept new users.

As used herein, the adverb "substantially" modifying an adjective means that a shape, structure, measurement, value, calculation, etc. may deviate from an exact described geometry, distance, measurement, value, calculation, etc., because of imperfections in materials, machining, manufacturing, sensor measurements, computations, processing time, communications time, etc.

Computing devices 105 generally each include instructions executable by one or more computing devices such as those identified above, and for carrying out blocks or steps of processes described above. Computer-executable instructions may be compiled or interpreted from computer programs created using a variety of programming languages and/or technologies, including, without limitation, and either alone or in combination, Java™, C, C++, Visual Basic, Java Script, Perl, HTML, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media. A file in the computing device 105 is generally a collection of data stored on a computer readable medium, such as a storage medium, a random access memory, etc.

A computer-readable medium includes any medium that participates in providing data (e.g., instructions), which may be read by a computer. Such a medium may take many forms, including, but not limited to, non-volatile media, volatile media, etc. Non-volatile media include, for example, optical or magnetic disks and other persistent memory. Volatile media include dynamic random access memory (DRAM), which typically constitutes a main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

With regard to the media, processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. For example, in the process 300, one or more of the steps could be omitted, or the steps could be executed in a different order than shown in FIG. 10. In other words, the descriptions of systems and/or processes herein are provided for the purpose of illustrating certain embodiments, and should in no way be construed so as to limit the disclosed subject matter.

Accordingly, it is to be understood that the present disclosure, including the above description and the accompanying figures and below claims, is intended to be illustrative and not restrictive. Many embodiments and applications other than the examples provided would be apparent to those of skill in the art upon reading the above description. The scope of the invention should be determined, not with reference to the above description, but should instead be determined with reference to claims appended hereto and/or included in a non-provisional patent application based hereon, along with the full scope of equivalents to which such claims are entitled. It is anticipated and intended that future developments will occur in the arts discussed herein, and that the disclosed systems and methods will be incorporated into such future embodiments. In sum, it should be understood that the disclosed subject matter is capable of modification and variation.

The invention claimed is:

1. A system, comprising:
    a vehicle seat including a seat back and a seat bottom;
    a track disposed in the seat along at least one of the seat back and the seat bottom;
    an actuator movably connected to the track;
    a cleaning apparatus including an arm and a bar, the arm connected to the actuator and the bar rotatably connected to the arm; and
    a computing device including a processor and a memory, the processor programmed to actuate the actuator to move the arm along the track and to push at least one object off of the vehicle seat onto a vehicle floor.

2. The system of claim 1, further comprising a vacuum device arranged to apply a vacuum to move the object from the vehicle floor to a container.

3. The system of claim 2, wherein the at least one of the container and the seat includes a port, the vacuum device arranged to apply the vacuum across the port to move the object from the vehicle floor to the container.

4. The system of claim 2, wherein the container includes a storage bin, the vacuum device arranged to move the object from the vehicle floor to the storage bin.

5. The system of claim 1, wherein the arm includes at least one nozzle arranged to spray a cleaning fluid onto the vehicle seat.

6. The system of claim 5, further comprising a fan arranged to dry the cleaning fluid on the vehicle seat.

7. The system of claim 1, wherein the vehicle seat includes a second actuator arranged to rotate the seat bottom to a predetermined angle to move the object from the seat bottom to the vehicle floor.

8. The system of claim 7, further comprising a movable bin, a second track disposed in the vehicle floor extending beneath the vehicle seat, and a third actuator movably connected to the second track, the third actuator arranged to move the movable bin along the second track to collect the object from the seat bottom.

9. The system of claim 1, further comprising a second track disposed in a vehicle pillar, a second arm rotatably connected to the bar, and a second actuator movably connected to the track and to the second arm.

10. The system of claim 9, wherein the second arm includes a plurality of telescopically connected sections, and the system includes a third actuator arranged to extend at least one of the telescopically connected sections.

11. A system, comprising a computer including a processor and a memory, the memory storing instructions executable by the computer to:
    rotate a rotatable seat bottom of a vehicle seat to move at least one object to a vehicle floor;
    actuate a cleaning apparatus installed in a vehicle to move the at least one object from the vehicle floor to a container in the vehicle; and
    spray the vehicle seat with a cleaning fluid.

12. The system of claim 11, wherein the cleaning apparatus includes a vacuum device.

13. The system of claim 12, wherein the vacuum device is connected to the container.

14. The system of claim 11, wherein the instructions further include instructions to determine that the vehicle is unoccupied and to actuate the cleaning apparatus only when the vehicle is unoccupied.

15. The system of claim 11, wherein the container includes a compactor, a cavity opening to the compactor, and at least one port connected to the compactor.

16. The system of claim 11, wherein the instructions further include instructions to control a vacuum generator to move the object from the vehicle floor to a storage bin through a port.

17. The system of claim 11, wherein the cleaning apparatus includes at least one arm and a bar extending from the arm.

18. The system of claim 17, wherein the cleaning apparatus further includes at least one nozzle supported by the bar and a sanitizer supply supported by the bar.

19. A vehicle, comprising:
- a seat including a seat back and a seat bottom;
- a floor;
- a track disposed in the seat along at least one of the seat back and the seat bottom;
- an actuator movably connected to the track;
- a cleaning apparatus including an arm, a bar, and a nozzle, the arm connected to the actuator and the bar rotatably connected to the arm and the nozzle supported by the bar; and
- a container including a vacuum device and a storage bin;
- wherein the cleaning apparatus is arranged to push at least one object off of the seat and onto the floor;
- wherein the nozzle is arranged to spray a cleaning fluid onto the seat;
- wherein the vacuum device is arranged to move the object from the floor to the storage bin.

* * * * *